United States Patent [19]

Findeisen et al.

[11] Patent Number: 4,931,084
[45] Date of Patent: Jun. 5, 1990

[54] HERBICIDAL SUBSTITUTED TRIAZOLINONES

[75] Inventors: Kurt Findeisen, Odenthal; Markus Lindig, Hilden; Hans-Joachim Santel, Leverkusen; Robert R. Schmidt, Bergisch-Gladbach; Harry Strang, Duesseldorf, all of Fed. Rep. of Germany

[73] Assignee: Bayer Aktiengesellschaft, Leverkusen, Fed. Rep. of Germany

[21] Appl. No.: 233,691

[22] Filed: Aug. 18, 1988

[30] Foreign Application Priority Data

Sep. 1, 1987 [DE] Fed. Rep. of Germany ....... 3729070

[51] Int. Cl.$^5$ ................. A01N 43/653; C07D 249/12
[52] U.S. Cl. ........................................... 71/92; 71/88; 71/94; 71/95; 548/518; 548/519; 548/263.4; 548/263.8; 546/210; 544/132; 544/366; 540/603
[58] Field of Search ........................ 71/88, 92, 94, 95; 546/210; 540/603; 544/132, 366; 548/262, 263, 265, 518, 519

[56] References Cited

FOREIGN PATENT DOCUMENTS 2707801 1/1977 Fed. Rep. of Germany ...... 548/265

OTHER PUBLICATIONS

Bany, T. et al., "Derivatives of 1,2,4-triozole-5-thione, etc." CA87:135170X (1977).
Rudnicka et al., "Reaction of 1,2,4-Triazole-3-Thione, etc." CA 89:6283d (1978).
Iwai et al.,"Triazoline Derivatives" CA90:152195p (1979).
Rudnicka et al., "Some Derivatives, etc." CA95:203841j (1981).

Primary Examiner—Glennon H. Hollrah
Assistant Examiner—Patricia L. Morris
Attorney, Agent, or Firm—Sprung Horn Kramer & Woods

[57] ABSTRACT

Herbicidal substituted triazolinones of the formula

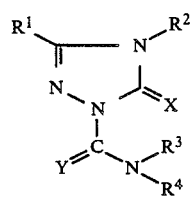
(I)

in which
$R^1$ stands for a

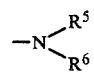

radical or for a —S(O)$_n$—R$^7$ radical,
in which
$R^5$ and $R^6$ independently of one another in each case stand for alkyl, alkenyl, alkynyl, halogenoalkyl, halogenoalkenyl, halogenoalkynyl, alkoxyalkyl, alkoxy, cycloalkyl, cycloalkylalkyl, for in each case optionally substituted aryl, aralkyl or heteroaryl, or together with the nitrogen atom to which they are bonded, stand for an optionally substituted heterocyclic ring,
$R^7$ stands for alkyl, alkenyl, alkynyl, cycloalkyl, cycloalkylalkyl or for in each case optionally substituted aralkyl or aryl, and
n stands for the number 0, 1 or 2,
$R^2$ stands for alkyl, alkenyl, alkinyl, halogenoalkyl, halogenoalkenyl, halogenoalkynyl, alkoxyalkyl, alkoxy, cycloalkylalkyl, cycloalkyl or for in each case optionally substituted aralkyl or aryl,
$R^3$ stands for hydrogen or alkyl,
$R^4$ stands for alkoximinolkyl,
X stands for oxygen or sulphur and
Y stands for oxygen or sulphur.

New intermediates of the formula

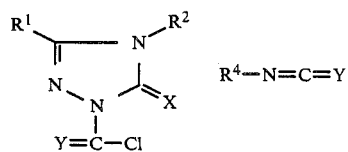

are also provided.

7 Claims, No Drawings

HERBICIDAL SUBSTITUTED TRIAZOLINONES

The invention relates to new substituted triazolinones, several processes for their preparation and their use as herbicides.

It has been disclosed that certain nitrogen heterocycles such as, for example, N-isobutylimidazolidin-2-one-1-carboxamide (compare, for example, K. H. Büchel "Pflanzenschutz and Schädlingsbekämpfung" ("Plant Protection and Pest Control") page 170, Thieme Verlag Stuttgart 1977) possess herbicidal properties.

However, the herbicidal activity of these previously known compounds with respect to problem weeds, like their tolerability with respect to important cultivated plants, is not completely satisfactory in all areas of application.

New substituted triazolinones of the general formula (I)

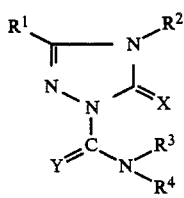

in which
$R^1$ stands for a

radical or for a $-S(O)_n-R^7$ radical,
in which
$R^5$ and $R^6$ independently of one another in each case stand for alkyl, alkenyl, alkinyl, halogenoalkyl, halogenoalkenyl, halogenoalkinyl, alkoxyalkyl, alkoxy, cycloalkyl, cycloalkylalkyl, for in each case optionally substituted aryl, aralkyl or heteroaryl, or together with the nitrogen atom to which they are bonded, stand for an optionally substituted heterocyclic ring,
$R^7$ stands for alkyl, alkenyl, alkinyl, cycloalkyl, cycloalkylalkyl or for in each case optionally substituted aralkyl or aryl, and
n stands for the number 0, 1 or 2,
$R^2$ stands for alkyl, alkenyl, alkinyl, halogenoalkyl, halogenoalkenyl, halogenoalkinyl, alkoxyalkyl, alkoxy, cycloalkylalkyl, cycloalkyl or for in each case optionally substituted aralkyl or aryl,
$R^3$ stands for hydrogen or alkyl,
$R^4$ stands for alkoximinoalkyl,
X stands for oxygen or sulphur and
Y stands for oxygen or sulphur, have been found.

Furthermore, it has been found that the new substituted triazolinones of the general formula (I)

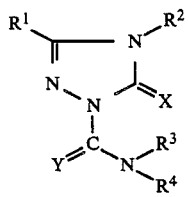

in which
$R^1$ stands for a

radical or for a $-S(O)_n-R^7$ radical,
in which
$R^5$ and $R^6$ independently of one another in each case stand for alkyl, alkenyl, alkinyl, halogenoalkyl, halogenoalkenyl, halogenoalkinyl, alkoxyalkyl, alkoxy, cycloalkyl, cycloalkylalkyl, for in each case optionally substituted aryl, aralkyl or heteroaryl, or together with the nitrogen atom to which they are bonded, stand for an optionally substituted heterocyclic ring,
$R^7$ stands for alkyl, alkenyl, alkinyl, cycloalkyl, cycloalkylalkyl or for in each case optionally substituted aralkyl or aryl, and
n stands for the number 0, 1 or 2,
$R^2$ stands for alkyl, alkenyl, alkinyl, halogenoalkyl, halogenoalkenyl, halogenoalkinyl, alkoxyalkyl, alkoxy, cycloalkylalkyl, cycloalkyl or for in each case optionally substituted aralkyl or aryl,
$R^3$ stands for hydrogen or alkyl,
$R^4$ stands for alkoximinoalkyl,
X stands for oxygen or sulphur and
Y stands for oxygen or sulphur, are obtained when
(a) 1-chloro-(thio)-carbonyltriazolinones of the formula (II)

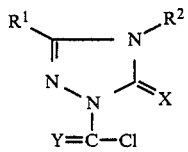

in which
$R^1$, $R^2$, X and Y have the abovementioned meaning, are reacted with amines of the formula (III)

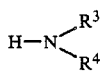

in which
$R^3$ and $R^4$ have the abovementioned meaning, if appropriate in the presence of a diluent and if appropriate in the presence of an acid-binding agent, or
(b) for the case in which $R^3$ denotes hydrogen, when 1-unsubstituted triazolinones of the formula (IV)

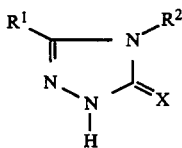

in which
R¹, R² and X have the abovementioned meaning, are reacted with iso(thio)cyanates of the formula (V)

R⁴—N=C=Y     (V)

in which
R⁴ and Y have the abovementioned meaning, if appropriate in the presence of a diluent and if appropriate in the presence of a reaction auxiliary.

Finally, it has been found that the new substituted triazolinones of the general formula (I) possess herbicidal properties.

Surprisingly, the substituted triazolinones of the general formula (I) according to the invention show a considerably higher herbicidal potency with respect to problem weeds than the nitrogen heterocyclic rings known from the prior art, such as, for example, imidazolin-2-one-1-carboxylic acid isobutylamide, which are closely related compounds chemically and with respect to their action.

Formula (I) provides a general definition of the substituted triazolinones according to the invention. Preferred compounds of the formula (I) are those in which
R¹ stands for a

radical or for a —S(O)ₙ—R⁷ radical,
in which
R⁵ and R⁶ independently of one another in each case stand for in each case straight-chain or branched alkyl having 1 to 8 carbon atoms, alkenyl having 2 to 8 carbon atoms, alkinyl having 2 to 8 carbon atoms, halogenoalkyl having 1 to 8 carbon atoms and 1 to 17 identical or different halogen atoms, halogenoalkenyl having 2 to 8 carbon atoms and 1 to 13 identical or different halogen atoms, halogenoalkynyl having 2 to 8 carbon atoms and 1 to 13 identical or different halogen atoms, or alkoxyalkyl or alkoxy each having 1 to 6 carbon atoms in the individual alkyl parts, for cycloalkyl having 3 to 7 carbon atoms, for cycloalkylalkyl having 3 to 7 carbon atoms in the cycloalkyl part and 1 to 6 carbon atoms in the alkyl part or for aralkyl having 6 to 10 carbon atoms in the aryl part and 1 to 6 carbon atoms in the alkyl part, or stand for aryl having 6 to 10 carbon atoms or heteroaryl having 2 to 9 carbon atoms and 1 to 3 hetero atoms, in particular nitrogen, oxygen and/or sulphur, which are in each case optionally monosubstituted or polysubstituted by identical or different substituents, suitable substituents in each case being: halogen, cyano, nitro, in each case straight-chain or branched alkyl, alkoxy, alkylthio, halogenoalkyl, halogenoalkoxy or halogenoalkylthio each having 1 to 4 carbon atoms and, where appropriate, 1 to 9 identical or different halogen atoms, or R⁵ and R⁶, together with the nitrogen atom to which they are bonded, stand for a five- to ten-membered heterocyclic ring, which can optionally contain 1 to 2 additional hetero atoms, in particular nitrogen, oxygen and/or sulphur, which is optionally monosubstituted or polysubstituted by identical or different substituents, suitable substituents being: halogen, in each case straight-chain or branched alkyl or halogenoalkyl each having 1 to 4 carbon atoms and, where appropriate, 1 to 9 identical or different halogen atoms and also 1 to 2 oxo or thiono groups, R⁷ stands for in each case straight-chain or branched alkyl having 1 to 8 carbon atoms, alkenyl having 2 to 8 carbon atoms, or alkinyl having 2 to 8 carbon atoms, for cycloalkyl having 3 to 7 carbon atoms, for cycloalkylalkyl having 3 to 7 carbon atoms in the cycloalkyl part and 1 to 6 carbon atoms in the alkyl part, for aralkyl having 6 to 10 carbon atoms in the aryl part and 1 to 6 carbon atoms in the alkyl part or for aryl having 6 to 10 carbon atoms, which are each optionally monosubstituted or polysubstituted by identical or different substituents, suitable aryl substituents in each case being: halogen, cyano, nitro and also in each case straight-chain or branched alkyl, alkoxy or halogenoalkyl each having 1 to 4 carbon atoms and, where appropriate, 1 to 9 identical or different halogen atoms, and
n stands for the number 0, 1 or 2,
R² stands for in each case straight-chain or branched alkyl having 1 to 8 carbon atoms, alkenyl having 2 to 8 carbon atoms, alkinyl having 2 to 8 carbon atoms, halogenoalkyl having 1 to 8 carbon atoms and 1 to 17 identical or different halogen atoms, halogenoalkenyl having 2 to 8 carbon atoms and 1 to 15 identical or different halogen atoms, halogenoalkinyl having 2 to 8 carbon atoms and 1 to 13 identical or different halogen atoms, or alkoxyalkyl or alkoxy each having 1 to 6 carbon atoms in the individual alkyl parts, for cycloalkylalkyl or cycloalkyl each having 3 to 7 carbon atoms in the cycloalkyl part and, where appropriate, 1 to 6 carbon atoms in the straight-chain or branched alkyl part or for aralkyl or aryl each having 6 to 10 carbon atoms in the aryl part and, where appropriate, 1 to 6 carbon atoms in the straight-chain or branched alkyl part, each of which is optionally monosubstituted or polysubstituted by identical or different substituents, suitable aryl substituents being: halogen, cyano, nitro, and also in each case straight-chain or branched alkyl, alkoxy, alkylthio, halogenoalkyl, halogenoalkoxy or halogenoalkylthio each having 1 to 4 carbon atoms and, where appropriate, 1 to 9 identical or different halogen atoms,
R³ stands for hydrogen or for straight-chain or branched alkyl having 1 to 8 carbon atoms,
R⁴ stands for straight-chain or branched alkoximinoalkyl each having 1 to 8 carbon atoms in the individual alkyl parts,
X stands for oxygen or sulphur and
Y stands for oxygen or sulphur.

Particularly preferred compounds of the formula (I) are those in which
R¹ stands for a

radical or for a —S(O)ₙ—R⁷ radical,
in which
R⁵ and R⁶ independently of one another in each case stand for methyl, ethyl, n- or i-propyl, n-, i-, s- or t-butyl, n- or i-pentyl, allyl, propargyl, for in each case straight-chain or branched halogenoalkyl having 1 to 4 carbon atoms, halogenoalkenyl having 3 to 6 carbon atoms or halogenoalkinyl having 3 to 6 carbon atoms and in each case 1 to 9 identical or different halogen atoms, for methoxymethyl, methoxyethyl, methoxy or ethoxy, for cyclopropyl, cyclopentyl, cyclohexyl, cyclopropylmethyl, cyclopentylmethyl, cyclohexylmethyl or cyclohexylethyl, or for benzyl, phenylethyl or phenyl which are in each case optionally monosubstituted, disubstituted or trisubstituted by identical or different substituents, suitable substituents being: fluorine, chlorine, bromine, cyano, nitro, methyl, ethyl, n- or i-propyl, n-, i-, s- or t-butyl, methoxy, ethoxy, methylthio, trifluoromethyl, trifluoromethoxy or trifluoromethylthio, or $R^5$ and $R^6$, together with the nitrogen atom to which they are bonded, stand for a heterocyclic ring of the formula

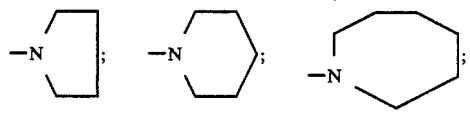

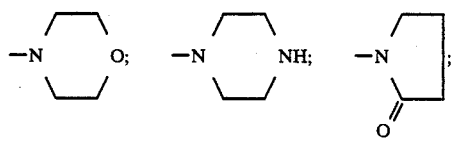

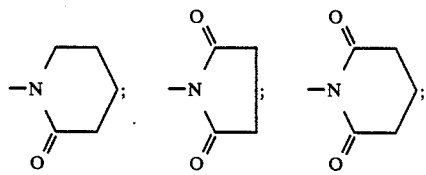

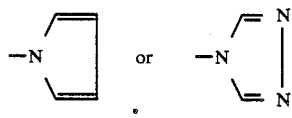

which is optionally monosubstituted to trisubstituted by identical or different substituents, suitable substituents being: methyl, ethyl, n- or i-propyl, chlorine or trifluoromethyl, $R^7$ stands for methyl, ethyl, n- or i-propyl, n-, i-, s- or t-butyl, allyl, propargyl, cyclopentyl, cyclohexyl, cyclohexylmethyl or cyclohexylethyl, or for benzyl or phenyl which are in each case optionally monosubstituted, disubstituted or trisubstituted by identical or different substituents, suitable substituents in each case being: fluorine, chlorine, bromine, cyano, nitro, methyl, ethyl, n- or i-propyl, n-, i-, s- or t-butyl, methoxy, ethoxy or trifluoromethyl and n stands for the number 0, 1 or 2, $R^2$ stands for methyl, ethyl, n- or i-propyl, n-, i-, s- or t-butyl, n- or i-pentyl, or n- or i-hexyl, for allyl, propargyl, methoxy, ethoxy or methoxymethyl, for straight-chain or branched halogenoalkyl having 1 to 4 carbon atoms and 1 to 9 identical or different halogen atoms, in particular fluorine, chlorine or bromine, for cyclopropyl, cyclopentyl, cyclohexyl, cyclopropylmethyl, cyclohexylmethyl or cyclohexylethyl, or for benzyl or phenyl which are in each case optionally monosubstituted, disubstituted or trisubstituted by identical or different substituents, suitable substituents being: fluorine, chlorine, bromine, cyano, nitro, methyl, ethyl, n- or i-propyl, n-, i-, s- or t-butyl, methoxy, ethoxy, methylthio, trifluoromethyl, trifluoromethoxy or trifluoromethylthio, $R^3$ stands for hydrogen, methyl, ethyl, n- or i-propyl, or n-, i-, s- or t-butyl, $R^4$ stands for straight-chain or branched alkoximinoalkyl in each case having 1 to 5 carbon atoms in the individual alkyl parts, X stands for oxygen or sulphur and Y stands for oxygen or sulphur.

Very particularly preferred compounds of the (I) formula are those in which $R^1$ stands for a

radical or for a —S(O)$_n$—R$^7$ radical, in which $R^5$ and $R^6$ independently of one another in each case stands for methyl, ethyl, n- or i-propyl, or n-, i-, s- or t-butyl, for allyl, propargyl, methoxymethyl, cyclohexyl, benzyl or phenyl, or, together with the nitrogen atom to which they are bonded, stand for a heterocyclic ring of the formula

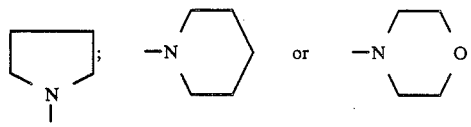

$R^7$ stands for methyl, ethyl, n- or i-propyl, n-, i-, s- or t-butyl, for allyl, propargyl, benzyl or phenyl and n stands for 0, $R^2$ stands for methyl, ethyl, n- or i-propyl, n-, i-, s- or t-butyl, for cyclohexyl, benzyl or phenyl, $R^3$ stands for hydrogen, $R^4$ stands for in each case optionally straight-chain or branched methoximinomethyl, ethoximinomethyl, methoximinoethyl, ethoximinoethyl, propoximinoethyl, methoximinopropyl, ethoximinopropyl, propoximinopropyl, methoximinobutyl, ethoximinobutyl, propoximinobutyl, methoximinopentyl, ethoxyiminopentyl or propoximinopentyl, X stands for oxygen or sulphur and Y stands for oxygen or sulphur.

The following substituted triazolinones of the general formula (I)

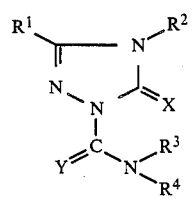

may be mentioned individually in addition to the compounds mentioned in the preparation examples:

TABLE 1

| R¹ | R² | X | Y | $-N{<}^{R^3}_{R^4}$ |
|---|---|---|---|---|
| $-N(CH_3)_2$ | CH₃ | O | O | $-NH-CH_2-CH=N-OCH_3$ |
| $-N(CH_3)_2$ | CH₃ | O | O | $-NH-C(CH_3)_2-CH=N-OCH_3$ |
| $-N(CH_3)_2$ | CH₃ | O | O | $-NH-CH(CH_3)-CH=N-OC_2H_5$ |
| $-N(C_2H_5)_2$ | CH₃ | O | O | $-NH-CH_2-CH=N-OCH_3$ |
| $-N(CH_3)_2$ | C₂H₅ | O | O | $-NH-CH(CH_3)-CH=N-OCH_3$ |
| $-N(CH_3)_2$ | CH₃ | O | O | $-NH-C(CH_3)_2-CH=N-OCH_3$ |
| $-N(CH_3)_2$ | CH₃ | O | O | $-NH-CH(CH_3)-C(CH_3)=N-OCH_3$ |
| $-N(CH_3)_2$ | CH₃ | O | O | $-NH-CH_2-C(CH_3)_2-CH=N-OCH_3$ |
| $-N(CH_3)_2$ | CH₃ | O | O | $-NH-C(CH_3)_2-CH=N-OC_2H_5$ |
| $-SCH_3$ | CH₃ | O | O | $-NH-C(CH_3)_2-CH=N-OCH_3$ |
| $-SCH_3$ | CH₃ | S | O | $-NH-CH(CH_3)-CH=N-OCH_3$ |
| $-N(CH_3)_2$ | CH₃ | O | O | $-NH-(CH_2)_3-CH=N-OCH_3$ |
| $-N(CH_3)_2$ | CH₃ | O | O | $-NH-(CH_2)_4-CH=N-OCH_3$ |
| $-N(CH_3)_2$ | CH₃ | O | O | $-NH-C(CH_3)_2-CH_2-CH=N-OCH_3$ |
| $-N(CH_3)_2$ | CH₃ | O | O | $-NH-CH(CH_3)-CH(CH_3)-CH=N-OCH_3$ |

If, for example, 1-chlorocarbonyl-3-dimethylamino-4-methyl-1,2,4-triazolin-5-one and 1-methyl-2-methoximino-ethylamine are used as starting materials, then the course of the reaction of process (a) according to the invention can be represented by the following equation:

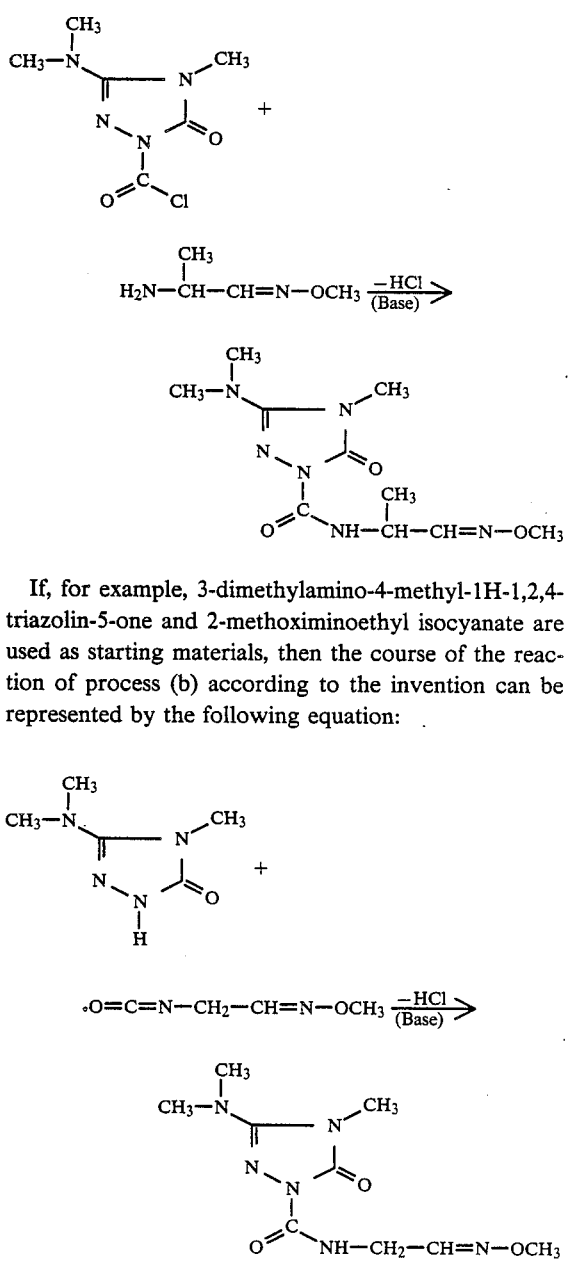

If, for example, 3-dimethylamino-4-methyl-1H-1,2,4-triazolin-5-one and 2-methoximinoethyl isocyanate are used as starting materials, then the course of the reaction of process (b) according to the invention can be represented by the following equation:

Formula (II) provides a general definition of the chloro(thio)carbonyltriazolinones required as starting materials for carrying out process (a) according to the invention. In this formula (II), R¹, R², X and Y preferably or particularly preferably stand for those radicals which have already been mentioned as preferred or particularly preferred for these substituents in connection with the description of the substances of the formula (I) according to the invention.

The chloro(thio)carbonyltriazolinones of the formula (II) were hitherto unknown.

They are obtained when 1-unsubstituted triazolinones of the formula (IV)

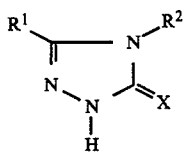  (IV)

in which

R[1], R[2] and X have the abovementioned meaning, are reacted with (thio)phosgene of the formula (VI)

  (VI)

in which

Y has the abovementioned meaning, if appropriate in the presence of a diluent such as, for example, toluene or acetonitrile and if appropriate in the presence of an acid-binding agent such as, for example, triethylamine, at temperatures between $+20°$ C. and $+150°$ C.

Chloro(thio)carbonyl compounds of the formula (IIa)

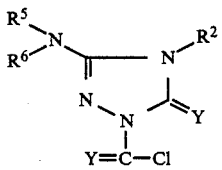  (IIa)

in which

R[2], R[5], R[6] and Y have the abovementioned meaning, are alternatively also obtained when aminoguanidinium hydrochlorides of the formula (VII)

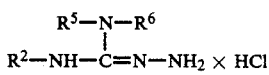  (VII)

in which

R[2], R[5] and R[6] have the abovementioned meaning, are reacted with a two-fold molar excess of (thio)phosgene of the formula (VI)

  (VI)

in which

Y has the abovementioned meaning, if appropriate in the presence of a diluent such as, for example, toluene or acetonitrile and if appropriate in the presence of an acid-binding agent such as, for example, triethylamine, at temperatures between $+20°$ C. and $+150°$ C.

The aminoguanidinium hydrochlorides of the formula (VII) are obtained in analogy to known processes, for example when the generally known ureas of the formula (VIII)

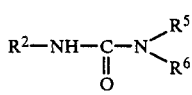  (VIII)

in which

R[2], R[5] and R[6] have the abovementioned meaning, are reacted in a 1st step with (thio)phosgene of the formula (VI)

  (VI)

in which

Y has the abovementioned meaning, if appropriate in the presence of a diluent such as, for example, toluene or acetonitrile, at temperatures between $+10°$ C. and $+150°$ C., and the formamidine hydrochlorides of the formula (IX)

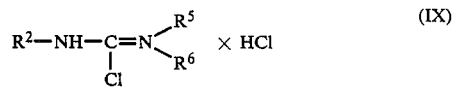  (IX)

in which

R[2], R[5] and R[6] have the abovementioned meaning, thus obtainable are reacted in a 2nd step with hydrazine hydrate, if appropriate in the presence of a diluent such as, for example, isopropanol or dichloromethane, at temperatures between $-10°$ C. and $+60°$ C. (compare, for example, J. org. Chem. 19, 1807 [1954]; Bull. Soc. Chim. Fr. 1975, 1649; U.S. Pat. No. 2,845,458).

Ureas of the formula (VIII) and phosgene or thiophosgene of the formula (VI) are generally known compounds of organic chemistry.

Formula (III) provides a general definition of the amines furthermore required as starting materials for carrying out process (a) according to the invention. In this formula (III), R[3] and R[4] preferably stand for those radicals which have already been mentioned as preferred for these substituents in connection with the description of the substances of the formula (I) according to the invention.

The amines of the formula (III) are known or obtainable in analogy to known processes (compare, for example, DE-OS (German Published Specification) 3,306,197).

Formula (IV) provides a general definition of the 1-unsubstituted triazolinones required as starting materials for carrying out process (b) according to the invention and for the synthesis of the precursors of the formula (II). In this formula (IV), R[1], R[2] and X preferably stand for those radicals which have already been mentioned as preferred for these substituents in connection with the description of the substances of the formula (I) according to the invention.

Some of the 1-unsubstituted triazolinones of the formula (IV) are known (compare, for example, Chem. Ber. 102, 735 [1969]; Chem. Ber. 107, 454 [1974]; Arch. Pharm. 307, 509 [1974]; Helv. Chim. Acta 63, 841 [1980]; U.S. Pat. Nos. 4,098,896; 4,110,332; 4,530,898; DE-OS (German Published Specification) 2,250,572; J. Chem. Soc. C. 1967, 746; J. Chem. Soc. Perkin Trans. I, 1059 [1982]; Arzneimittel Forsch. 27, 343 [1977]; Compt. Rend. 253, 1974 [1961]; Bull. Soc. Chim. Fr. 1963, 144; and French Patent FR M 1559 of 3.12.62). The known, as well as the unknown, compounds of the formula (IV) are obtained in analogy to known processes (compare, for example, J. org. Chem. 51, 1719 [1986]; U.S. Pat. No. 4,098,896 and also the preparation examples).

1-Unsubstituted triazolinones of the formula (IVa)

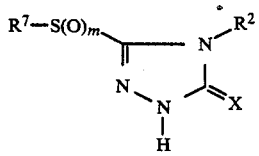

in which

R², R⁷ and X have the abovementioned meaning and m stands for the number 1 or 2, are obtained from the corresponding compounds of the formula (IVb)

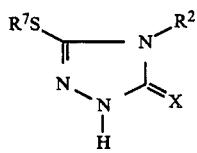

in which

R², R⁷ and X have the abovementioned meaning, in a generally known manner using customary oxidants, for example by reacting with 3-chloroperbenzoic acid, if appropriate in the presence of a diluent such as, for example, dichloromethane or acetonitrile and if appropriate in the presence of a catalyst such as, for example, ammonium molybdate, at temperatures between 0° C. and 40° C.

Formula (V) provides a general definition of the iso(thio)cyanates furthermore required as starting materials for carrying out process (b) according to the invention. In this formula (V), R⁴ and Y preferably stand for those radicals which have already been mentioned as preferred for these substituents in connection with the description of the substances of the formula (I) according to the invention.

The iso(thio)cyanates of the formula (V) were hitherto unknown. They are obtained in analogy to known processes (compare, for example, Saul Patai "The Chemistry of Cyanates and their Thio derivatives", John Wiley & Sons, New York 1977), for example when amines of the formula (III)

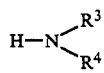

in which

R³ and R⁴ have the abovementioned meanings, are reacted with (thio)phosgene of the formula (VI)

in which

Y has the abovementioned meaning, if appropriate in the presence of a diluent such as, for example, toluene or chloroform and if appropriate in the presence of an acid-binding agent such as, for example, pyridine or triethylamine, at temperatures between 20° C. and 250° C.

Suitable diluents for carrying out process (a) according to the invention are preferably inert organic solvents.

In particular, these include aliphatic, alicyclic or aromatic, optionally halogenated hydrocarbons, such as, for example, benzine, ligroin, benzene, toluene, xylene, chlorobenzene, petroleum ether, pentane, hexane, heptane, cyclohexane, dichloromethane, chloroform, carbon tetrachloride, ethers, such as diethyl ether, dioxane, tetrahydrofuran or ethylene glycol dimethyl ether or ethylene glycol diethyl ether, ketones such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate or bases such as pyridine.

If desired, process (a) according to the invention is carried out in the presence of a suitable acid-binding agent.

Those which are suitable are all customary inorganic or organic bases. These include, for example, alkali metal hydroxides, such as sodium hydroxide or potassium hydroxide, alkali metal carbonates, such as sodium carbonate, potassium carbonate or sodium hydrogen carbonate, and also tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

It is also possible to employ the amine of the formula (III) used as the reaction partner in a suitable excess simultaneously as the acid-binding agent.

The reaction temperatures can be varied within a relatively wide range when carrying out process (a) according to the invention. In general, the process is carried out at temperatures between 0° C. and +150° C., preferably at temperatures between +10° C. and +80° C.

Process (a) according to the invention is conventionally carried out under atmospheric pressure. However, it is also possible to work at elevated pressure.

For carrying out process (a) according to the invention, 1.0 to 5.0 mols, preferably 1.0 to 2.5 mols, of amine of the formula (III) and if desired 1.0 to 2.5 mols of acid-binding agent are generally employed per mol of 1-chloro-(thio)carbonyl-triazolinone of the formula (II). The reaction is carried out, and the reaction products are worked up and isolated in analogy to generally known processes.

Suitable diluents for carrying out process (b) according to the invention are also inert organic solvents. The diluents mentioned in process (a) are preferably used.

If desired, process (b) can be carried out in the presence of a basic reaction auxiliary. Those which are suitable are all customary inorganic and organic bases. Tertiary amines, such as triethylamine, N,N-dimethylaniline, pyridine, N,N-dimethylaminopyridine, diazabicyclooctane (DABCO), diazabicyclononene (DBN) or diazabicycloundecene (DBU) are preferably used.

The addition of such catalysts is not compulsory, however.

The reaction temperatures can be varied within a relatively wide range when carrying out process (b) according to the invention. In general, the process is carried out at temperatures between 0° C. and +150° C., preferably at temperatures between +40° C. and +120° C.

Process (b) according to the invention is conventionally carried out under atmospheric pressure. However, it is also possible to work at elevated pressure.

For carrying out process (b) according to the invention, 1.0 to 5.0 mols, preferably 1.0 to 2.5 mols, of iso(- thio)cyanate of the formula (V) and, if desired, 1.0 to 2.5 mols of reaction auxiliary are generally employed per mol of 1-unsubstituted triazolinone of the formula (IV). The reaction is carried out, and the reaction products are worked up and isolated in analogy to generally known processes.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

In this case, the active compounds according to the invention can be used with particularly good success for combating dicotyledon weeds, in particular in monocotyledon cultures, such as wheat or maize.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Suitable components for the mixtures are known herbicides, such as, for example, 1-amino-6-ethylthio-3-(2,2-dimethylpropyl)-1,3,5-triazine-2,4(1H,3H)-dione or N-(2-benzothiazolyl)-N,N'-dimethylurea for combating weeds in cereals; 4-amino-3-methyl-6-phenyl-1,2,4-triazin-5(4H)-one for combating weeds in sugar beets, and 4-amino-6-(1,1-dimethylethyl)-3-methylthio-1,2,4-triazin-5(4H)-one for combating weeds in soy beans. Mixtures with 2,4-dichlorophenoxyacetic acid; 4-(2,4-dichlorophenoxy)butyric acid; 2,4-dichlorophenoxypropionic acid; 2-chloro-4-ethylamino-6-isopropylamino-1,3,5-triazine; 3-isopropyl-2,1,3-benzothiadiazin-4-one-2,2-dioxide; methyl 5-(2,4-dichlorophenoxy)-2-nitrobenzoate; 3,5-dibromo-4-hydroxy-benzonitrile; 2-chloro-N-{[(4-methoxy-6-methyl-1,3,5-triazin-2-yl)-amino]-carbonyl}-benzenesulphonamide; N,N-dimethyl-N'-(3-chloro-4-methylphenyl)urea; 2-chloro-4-ethylamino-6-(3-cyanopropylamino)-1,3,5-triazine; 2-[4-(2,4-dichlorophenoxy)-phenoxy]-propionic acid, its methyl or its ethyl ester; 3,6-dichloro-2-pyridinecarboxylic acid; S-ethyl N,N-di-n-propyl-thiocarbamate; 4-amino-6-t-butyl-3-ethylthio-1,2,4-triazin-5(4H)-one; 2-{4-[(6-chloro-2-benzoxazolyl)-oxy]-phenoxy}propanoic acid, its methyl or its ethyl ester; (trimethylsilylmethyl) 2-[4-(3,5-dichloropyrid-2-yloxy)-phenoxy]-propionate; methyl 2-[4,5-dihydro-4-methyl-4-(1-methylethyl)-5-oxo-1H-imidazol-2-yl]-4(5)-methyl-benzoate; N,N-dimethyl-N'-(4-isopropylphenyl)-urea; (2-methyl-4-chlorophenoxy)-acetic acid; (4-chloro-2-methylphenoxy)-propionic acid; N-methyl-2-(1,3-benzothiazol-2-yloxy)-acetanilide; 2-{[[((4-methoxy-6-methyl-1,3,5-triazin-2-yl)-amino)-carbonyl]-amino]-sulphonyl}-benzoic acid or its methyl ester; N-(1-ethylpropyl)-3,4-dimethyl-2,6-dinitroaniline; 0-(6-chloro-3-phenyl-pyridazin-4-yl) S-octylthiocarbonate; 4-ethylamino-2-t-butylamino-6-methylthio-s-triazine; methyl 3-[[[[(4-methoxy-6-methyl-1,3,5-triazin-2-yl)-amino]-carbonyl]-amino]-sulphonyl]thiophene-2-carboxylate; S-(2,3,3-trichloroallyl) N,N-diisoproyl-thiolcarbamate and 3,5,6-trichloro-2-pyridyloxyacetic acid are also possible. Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a relatively wide range. It depends essentially on the nature of the desired effect. In general, the amounts used are between 0.01 and 10 kg of active compound per hectare of soil surface, preferably between 0.05 and 5 kg per ha.

PREPARATION EXAMPLES

EXAMPLE 1

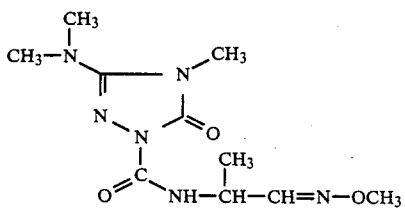
(Process (a))

4.1 g (0.04 mol) of 1-methoximino-2-propylamine are added dropwise to 4 g (0.02 mol) of 1-chlorocarbonyl-3-dimethylamino-4-methyl-1,2,4-triazolin-5-one in 100 ml of dichloromethane in such a way that the reaction temperature does not exceed 40° C. After completion of the addition, the mixture is stirred at room temperature for 12 hours, then washed twice with 100 ml of water and dried over sodium sulphate, and the solvent is removed in vacuo.

3.4 g (63% of theory) of 1-[N-(1-methoximino-2-propyl)-aminocarbonyl]-3-dimethylamino-4-methyl-1,2,4-triazolin-5-one are obtained as an oil.

$^1$H-NMR (CDCl$_3$/TMS): $\delta = 3.85$ ppm (OCH$_3$).

PREPARATION OF THE STARTING COMPOUNDS

EXAMPLE II-1

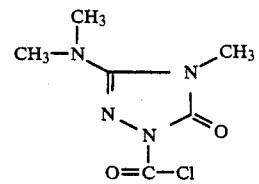

71 g (0.5 mol) of 3-dimethylamino-4-methyl-1H-1,2,4-triazolin-5-one in 300 ml of toluene are warmed to 120° C. while introducing phosgene. Altogether, 115 g (1.15 mol) of phosgene are introduced. From 80° C., a vigorous evolution of hydrogen chloride takes place. After completion of the phosgene introduction, the mixture is stirred for a further 5 hours at 120° C., excess phosgene and hydrogen chloride are removed by blowing out with nitrogen and the mixture is filtered at 20° C. The filtrate is stirred with 1 liter of cyclohexane, and the precipitated product is filtered off with suction, washed with cyclohexane and dried.

70 g (69% of theory) of 1-chlorocarbonyl-3-dimethylamino-4-methyl-1,2,4-triazolin-5-one of melting point 78° C.–80° C. are obtained.

EXAMPLE IV-1

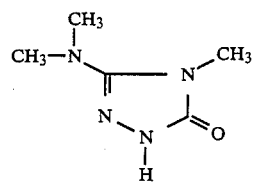

150 g (1.5 mols) of phosgene are introduced with stirring at 80° C. during the course of 2 hours into a suspension of 152.5 g (1 mol) of 1-amino-2,2,3-trimethylguanidinium hydrochloride in 1,000 ml of acetonitrile, the mixture is stirred at 80° C. for a further 30 minutes and cooled to 20° C., excess phosgene is removed by blowing out with nitrogen, the precipitated product is filtered off with suction and dissolved in 1,000 ml of water, and the solution is neutralized using concentrated sodium hydroxide solution and concentrated to dryness in vacuo. The oily residue is taken up in 1,000 ml of acetonitrile and filtered, and the filtrate is freed from solvent in vacuo.

80 g (57% of theory) of 3-dimethylamino-4-methyl-1H-1,2,4-triazolin-5-one of melting point 78° C.–80° C. are obtained.

EXAMPLE VII-1

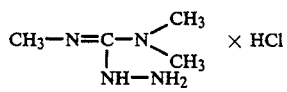

A solution of 78.5 g (0.5 mol) of chlorotrimethylformamidinium hydrochloride in 250 ml of isopropanol is added dropwise at 20° C. to 25° C. with stirring during the course of 30 minutes to 50 g (1 mol) of hydrazine hydrate in 300 ml of isopropanol, the mixture is stirred for a further 30 minutes at room temperature after completion of the addition, the precipitated hydrazine hydrochloride is filtered off with suction and washed with 150 ml of isopropanol, and the isopropanol filtrate is concentrated in vacuo.

70.7 g (93% of theory) of 1-amino-2,2,3-trimethylguanidinium hydrochloride are obtained, which reacted further without purification.

EXAMPLE IX-1

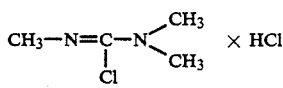

545 g (5.5 mols) of phosgene are introduced at 80° C. during the course of 2.5 hours with stirring into a mixture of 510 g (5 mols) of N,N,N'-trimethylurea and 3 liters of chlorobenzene and the mixture is stirred for a further 45 minutes after completion of the introduction until the end of carbon dioxide evolution at 80° C. The reaction mixture is cooled to 10° C., and the water-sensitive product is filtered off with suction under nitrogen, washed with 1 liter of chlorobenzene and twice with 500 ml of petroleum ether in each case and dried in vacuo.

635.3 g (81% of theory) of chlorotrimethylformamidinium hydrochloride of melting point 76° C. to 78° C. are obtained.

The following substituted triazolinones of the general formula (I)

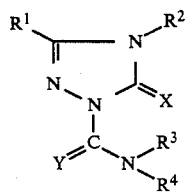

(I)

are obtained in a corresponding manner and according to the general instructions for the preparation:

USE EXAMPLE

The compound shown below was used as the comparison substance in the following use example:

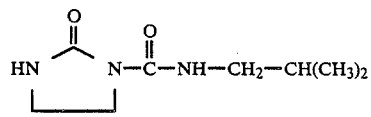

(A)

N-Isobutylimidazolidin-2-one-1-carboxamide (known from K. H. Büchel, "Pflanzenschutz and Schädlingsbekämpfung" ("Plant Protection and Pest Control") page 170, Thieme Verlag Stuttgart 1977)

EXAMPLE A

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is chosen so that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test, for example, the compound according to Preparation Example 1 shows a clear superiority in activity with comparable useful plant selectivity compared to the prior art.

It is understood that the specification and examples are illustrative but not limitative of the present invention and that other embodiments within the spirit and scope of the invention will suggest themselves to those skilled in the art.

We claim:
1. A substituted triazolinone of the formula

TABLE 2

| Ex. No. | $R^1$ | $R^2$ | X | Y | $-N\begin{smallmatrix}R^3\\R^4\end{smallmatrix}$ | Physical properties |
|---|---|---|---|---|---|---|
| 2 | $CH_3S-$ | $CH_3$ | O | O | $-NH-CH(CH_3)-CH=N-OCH_3$ | $^1$H-NMR*: 3.8 |
| 3 | $(CH_3)_2N-$ | $CH_3$ | O | O | $-NH-CH_2-CH=N-OCH_3$ | Oil |

*The $^1$H-NMR spectra were recorded in deuterochloroform (CDCl$_3$) using tetramethylsilane (TMS) as the internal standard. The chemical shift is given as the δ-value in ppm.

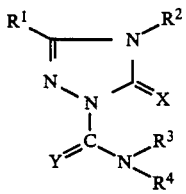
(I)

in which
R¹ stands for

radical or for a —S(O)$_n$—R⁷ radical
in which
R⁵ and R⁶ independently of one another in each case stand for in each case straight-chain or branched alkyl having 1 to 8 carbon atoms, alkenyl having 1 to 8 carbon atoms, alkynyl having 2 to 8 carbon atoms, halogenoalkyl having 1 to 8 carbon atoms and 1 to 17 identical or different halogen atoms, halogenoalkenyl having 2 to 8 carbon atoms and 1 to 15 identical or different halogen atoms, halogenoalkynyl having 2 to 8 carbon atoms and 1 to 13 identical or different halogen atoms, or alkoxyalkyl or alkoxy each having 1 to 6 carbon atoms in the individual alkyl parts, for cycloalkyl having 3 to 7 carbon atoms, for cycloalkylalkyl having 3 to 7 carbon atoms in the cycloalkyl part and 1 to 6 carbon atoms in the alkyl part or for aralkyl having 6 to 10 carbon atoms in the aryl part and 1 to 6 carbon atoms in the alkyl part, aryl having 6 to 10 carbon atoms, which are in each case optionally monosubstituted or polysubstituted by identical or different substituents selected from the group consisting of halogen, cyano, nitro and straight-chain or branched alkyl, alkoxy, alkylthio, halogenoalkyl, halogenoalkoxy or halogenoalkylthio each having 1 to 4 carbon atoms and 1 to 9 identical or different halogen atoms, or R⁵ and R⁶, together with the nitrogen atom to which they are bonded, stand for a heterocyclic ring selected from the group consisting of

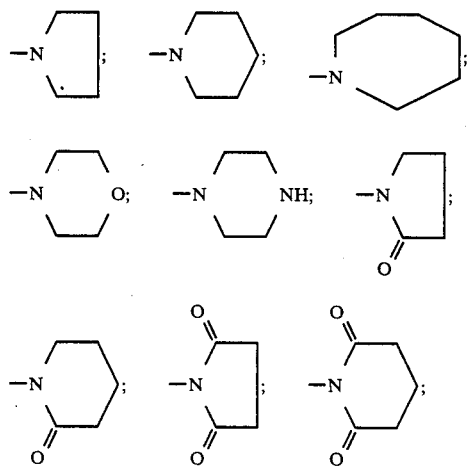

-continued

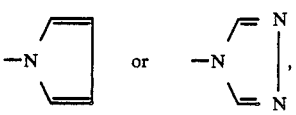

which is optionally monosubstituted or polysubstituted by identical or different substituents from the group consisting of halogen and alkyl or halogenoalkyl each having 1 to 4 carbon atoms and 1 to 9 identical or different halogen atoms and also 1 to 2 oxo or thiono groups, R⁷ stands for in each case straight-chain or branched alkyl having 1 to 8 carbon atoms, alkenyl having 2 to 8 carbon atoms, or alkynyl having 2 to 8 carbon atoms, for cycloalkyl having 3 to 7 carbon atoms, for cycloalkyalkyl having 3 to 7 carbon atoms in the cycloalkyl part and 1 to 6 carbon atoms in the alkyl part or for aralkyl having 6 to 10 carbon atoms in the aryl part and 1 to 6 carbon atoms in the alkyl part or aryl having 6 to 10 carbon atoms, which are each optionally substituted on the aryl by identical or different substituents selected from the the group consisting of halogen, cyano, nitro and straight-chain or branched alkyl, alkoxy or halogenoalkyl each having 1 to 4 carbon atoms and 1 to 9 identical or different halogen atoms, and n stands for the number 0, 1 or 2, R² stands for in each case straight-chain or branched alkyl having 1 to 8 carbon atoms, alkenyl having 2 to 8 carbon atoms, alkynyl having 2 to 8 carbon atoms, halogenoalkyl having 1 to 8 carbon atoms and 1 to 17 identical or different halogen atoms, halogenoalkenyl having 2 to 8 carbon atoms and 1 to 15 identical or different halogen atoms, halogenoalkynyl having 2 to 8 carbon atoms and 1 to 13 identical or different halogen atoms, or alkoxyalkyl or alkoxy each having 1 to 6 carbon atoms in the individual alkyl parts, for cycloalkylalkyl or cycloalkyl each having 3 to 7 carbon atoms in the cycloalkyl part and 1 to 6 carbon atoms in the straight-chain or branched alkyl part or for aralkyl or aryl each having 6 to 10 carbon atoms in the aryl part and 1 to 6 carbon atoms in the straight-chain or branched alkyl part, each of which is optionally substituted on the aryl by identical or different substituents selected from the group consisting of halogen, cyano, nitro, and also in each case straight-chain or branched alkyl, alkoxy, alkylthio, halogenoalkyl, halogenoalkoxy or halogenoalkylthio each having 1 to 4 carbon atoms and 1 to 9 identical or different halogen atoms, R³ stands for hydrogen or for straight-chain or branched alkyl having 1 to 8 carbon atoms, R⁴ stands for straight-chain or branched alkoximinoalkyl each having to 8 carbon atoms in the individual alkyl parts, X stands for oxygen or sulphur and Y stands for oxygen or sulphur.

2. A substituted triazolinone according to claim 1, in which

R⁵ and R⁶ independently of one another in each case stand for methyl, ethyl, n- or i-propyl, n-, i-, s- or t-butyl, n- or i-pentyl, allyl, propargyl, for in each case straight-chain or branched halogenoalkyl having 1 to 4 carbon atoms, halogenoalkenyl having 3 to 6 carbon atoms or halogenoalkynyl having 3 to 6 carbon atoms and in each case 1 to 9 identical or different halogen atoms, for methoxymethyl, methoxyethyl, methoxy or ethoxy, for cyclopropyl, cyclopentyl, cyclohexyl, cyclopropylmethyl, cyclopentylmethyl, cyclohexylmethyl or cyclohexylethyl, or for benzyl, phenylethyl or phenyl which are in each case optionally monosubstituted, disubstituted or trisubstituted by identical or different substituents from the group consisting of fluorine, chlorine, bromine, cyano, nitro, methyl, ethyl, n- or i-propyl, n-, i-, s- or t-butyl, methoxy, ethoxy, methylthio, trifluoromethyl, trifluoromethoxy and trifluoromethylthio, or $R^5$ and $R^6$, together with the nitrogen atom to which they are bonded, stand for a heterocyclic ring of the formula

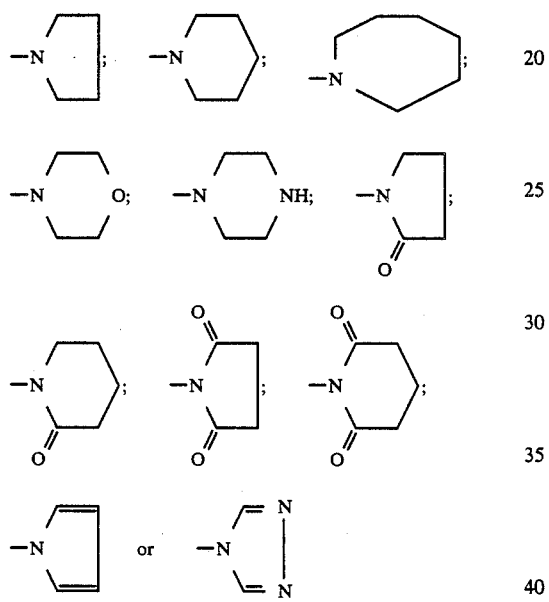

which is optionally monosubstituted to trisubstituted by identical or different substituents from the group consisting of methyl, ethyl, n- or i-propyl, chlorine or trifluoromethyl, $R^7$ stands for methyl, ethyl, n- or i-propyl, n-, i-, s- or t-butyl, allyl, propargyl, cyclopentyl, cyclohexyl, cyclohexylmethyl and cyclohexylethyl, or for benzyl or phenyl which are in each case optionally monosubstituted, disubstituted or trisubstituted by identical or different substituents from the group consisting of fluorine, chlorine, bromine, cyano, nitro, methyl, ethyl, n- or i-propyl, n-, i-, s- or t-butyl, methoxy, ethoxy and trifluoromethyl, $R^2$ stands for methyl, ethyl, n- or i-propyl, n-, i-, s- or t-butyl, n- or i-pentyl, or n- or i-hexyl, for allyl, propargyl, methoxy, ethoxy or methoxymethyl, for straight-chain or branched halogenoalkyl having 1 to 4 carbon atoms and 1 to 9 identical or different halogen atoms, for cyclopropyl, cyclopentyl, cyclohexyl, cyclopropylpropyl, cyclopentyl, cyclohexyl, cyclopropylmethyl, cyclohexylmethyl or cyclohexylethyl, or for benzyl or phenyl which are in each case optionally monosubstituted, disubstituted or trisubstituted by identical or different substituents from the group consisting of fluorine, chlorine, bromine, cyano, nitro, methyl, ethyl, n- or i-propyl, n-, i-, s- or t-butyl, methoxy, ethoxy, methylthio, trifluoromethyl, trifluoromethoxy and trifluoromethylthio, $R^3$ stands for hydrogen, methyl, ethyl, n- or i-propyl, or n-, i-, s- or t-butyl, $R^4$ stands for straight-chain or branched alkoximinoalkyl in each case having 1 to 5 carbon atoms in the individual alkyl parts.

3. A substituted triazolinone according to claim 1, in which $R^5$ and $R^6$ independently of one another in each case stand for methyl, ethyl, n- or i-propyl, or n-, i-, s- or t-butyl, for allyl, propargyl, methoxymethyl, cyclohexyl, benzyl or phenyl, or, together with the nitrogen atom to which they are bonded, stand for a heterocyclic ring of the formula

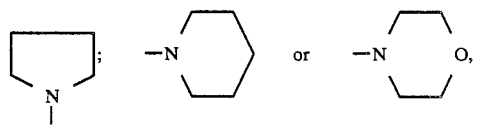

$R^7$ stands for methyl, ethyl, n- or i-propyl, n-, i-, s- or t-butyl, for allyl, propargyl, benzyl or phenyl, n stands for 0, $R^2$ stands for methyl, ethyl, n- or i-propyl, n-, i-, s- or butyl, for cyclohexyl, benzyl or phenyl, $R^3$ stands for hydrogen, and $R^4$ stands for methoximinomethyl, ethoximinomethyl, methoximinoethyl, ethoximinoethyl, propoximinoethyl, methoximinopropyl, ethoximinopropyl, propoximinopropyl, methoximinobutyl, ethoximinobutyl, propoximinobutyl, methoximinopentyl, ethoxyiminopentyl or propoximinopentyl.

4. A compound according to claim 2, wherein such compound is 1-[N-(1-methoximino-2-propyl)-aminocarbonyl]-3-dimethylamino-4-methyl-1,2,4-triazolin-5-one of the formula

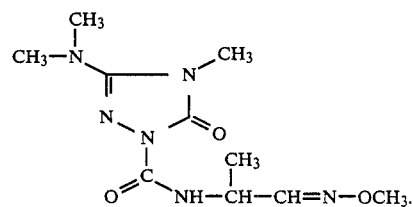

5. A herbicidal composition comprising a herbicidally effective amount of a compound according to claim 1 and an insert diluent.

6. A method of combating unwanted vegetation which comprises applying to such vegetation or to a locus from which it is desired to exclude such vegetation a herbicidally effective amount of a compound according to claim 1.

7. A method of combating unwanted vegetation which comprises applying to such vegetation or to a locus from which it is desired to exclude such vegetation a herbicidally effective amount of a compound according to claim 4.

* * * * *

UNITED STATES PATENT AND TRADEMARK OFFICE
CERTIFICATE OF CORRECTION

PATENT NO. : 4,931,084
DATED : June 5, 1990
INVENTOR(S) : Findeisen et al.

It is certified that error appears in the above-identified patent and that said Letters Patent is hereby corrected as shown below:

Title Page      FOREIGN PATENT DOCUMENTS: After " 2707801 " delete " 1/1977 " and substitute -- 9/1977 --

Title Page      ABSTRACT: Line 25 delete " alkoximinolkyl " and substitute -- alkoximinoalkyl --

Col. 22, claim 4 line 39      Delete " claim 2 " and substitute -- claim 1 --

Signed and Sealed this

Second Day of June, 1992

Attest:

DOUGLAS B. COMER

*Attesting Officer*      *Acting Commissioner of Patents and Trademarks*